US006156330A

United States Patent [19]

Tsukada et al.

[11] Patent Number: 6,156,330

[45] Date of Patent: Dec. 5, 2000

[54] CHITIN BEADS, CHITOSAN BEADS, PROCESS FOR PREPARING THESE BEADS, CARRIER COMPRISING SAID BEADS, AND PROCESS FOR PREPARING MICROSPORIDIAN SPORE

[75] Inventors: Masuhiro Tsukada; Akira Shirata; Sho Ji Hayasaka, all of Ttsukuba, Japan

[73] Assignee: Japan as represented by Director General of National Institute of Sericultural and Entomological Sciences Ministry of Agriculture, Forestry and Fisheries, Tsukuba, Japan

[21] Appl. No.: 09/214,383

[22] PCT Filed: Oct. 16, 1997

[86] PCT No.: PCT/JP97/03741

§ 371 Date: Dec. 30, 1998

§ 102(e) Date: Dec. 30, 1998

[87] PCT Pub. No.: WO98/51711

PCT Pub. Date: Nov. 19, 1998

[30] Foreign Application Priority Data

May 14, 1997 [JP] Japan .................................... 9-124255

[51] Int. Cl.$^7$ ............................ A01N 25/28; A01N 25/26

[52] U.S. Cl. .......................... 424/408; 424/405; 424/406; 424/418; 424/489; 424/493; 424/494; 424/499; 514/55

[58] Field of Search .................................... 424/405, 406, 424/408, 418, 489–494, 499; 435/85, 101; 514/55

[56] References Cited

U.S. PATENT DOCUMENTS 5,645,844 7/1997 Henderson et al. .................... 424/405

5,696,098 12/1997 Myraki ...................................... 514/55

5,885,603 3/1999 Fowler et al. .......................... 424/405

*Primary Examiner*—Neil S. Levy

*Attorney, Agent, or Firm*—Armstrong, Westerman, Hattori, McLeland & Naughton

[57] ABSTRACT

The present invention relates to chitin beads having a uniform and fine particle size and comprising microsporidian spores whose principal cell wall substance is chitin; chitosan beads comprising N-deacetylated chitin and having a uniform fine particle size; methods for preparing these beads; carriers comprising these beads; and a method for preparing microsporidian spores.

Microsporidian spores are proliferated in insect's bodies or cultured cells to obtain chitin beads having the uniform and fine particle size and whose cell wall substance is mainly composed of chitin. The chitin as the major cell wall substance is subjected to N-deacetylation to give chitosan beads. When the insect is a larva of domesticated silkworm, microsporidian spores are proliferated by orally or percutaneously inoculating the spores into the 2nd instar domesticated silkworm larvae in a concentration of $5\times10^2$ to $5\times10^8$ spores/ml, then the proliferated microsporidian spores are isolated from the bodies of the grown 5th instar domesticated silkworm larvae, followed by purifying the resulting spores to give chitin beads having the uniform and fine particle size and chitosan beads can be obtained from the chitin beads in the same manner used above. These beads are used as carriers for the immobilization or encapsulation of a variety of substances such as an antibiotic and a microorganism.

16 Claims, 1 Drawing Sheet

CHITIN BEADS, CHITOSAN BEADS, PROCESS FOR PREPARING THESE BEADS, CARRIER COMPRISING SAID BEADS, AND PROCESS FOR PREPARING MICROSPORIDIAN SPORE

TECHNICAL FIELD

The present invention relates to chitin beads having a uniform and fine particle size and comprising microsporidian spores whose major cell wall substance is chitin; chitosan beads comprising N-deacetylated chitin and having a uniform and fine particle size; methods for preparing these beads; carrier comprising these bead; and a method for preparing microsporidian spores.

BACKGROUND ART

Chitosan is excellent in physicochemical adsorptivity, biocompatibility and biodegradability and accordingly, the chitosan is a biopolymer which has been able to widely be used in various industrial fields as, for instance, a material for medicine/medical treatment, perfumes, cosmetics, adhesive/paints and varnishes, and duplication/recording-display. On the other hand, porous beads whose particle size does not widely vary have been used, as carriers for immobilization of, for instance, enzymes, in a wide variety of industrial fields such as chemical industries, medical treatments, food industries and industrial processes. For this reason, if porous beads of chitosan having a uniform particle size can be provided, they may be used and utilized in a variety of fields.

Chitosan beads have conventionally been produced by, for instance, the following complicated method. First of all, inorganic substances are removed from components which constitute the exoskeleton of crustaceans to give chitosan and then the resulting chitosan is sufficiently dissolved in an organic acid to form a uniform dope. This dope is dropwise added to or discharged into a basic coagulating liquid to thus give chitosan beads (see Knorr, D., M. Daly: Mechanics and diffusional changes observed in multi-layer chitosan/alginate coacervate capsules, Process Biochemistry, 1988, 4, pp. 48–50).

DISCLOSURE OF THE INVENTION

In the foregoing conventional method, the particle size and the porosity of the resulting chitosan beads would widely vary depending on, for instance, the rate of desolvation and rates of penetration and diffusion of the coagulating liquid into the resulting beads. For this reason, it is quite difficult to make the particle size of these beads uniform, thus the production of chitosan beads having the uniform particle size requires complicated preparation procedures and skill in the workers and this accordingly makes it difficult to effect mass production thereof. Thus, there has been desired for the development of a method for preparing chitosan beads having the uniform and fine particle size according to production procedures which can easily be carried out and can be excellent in yield, efficiency and economy.

The present invention has solved or eliminated the foregoing problems associated with the conventional techniques by making the most use of the fact that the spores of Microsporozoa having a uniform and fine particle size and whose major cell wall substance comprises chitin can highly efficiently be produced in insect's bodies or within cultured cells. More specifically, the object of the present invention is to provide a method for efficiently and economically preparing chitin beads, chitosan beads and microsporidian spores each having the uniform and fine particle size, while making use of the fact that chitin is the major component of the cell wall substance of particulate microsporidian spores, as well as the beads having the uniform and fine particle size prepared by the method and a carrier which comprises these beads having the uniform and fine particle size.

The inventors of the present invention have conducted intensive investigations to develop a novel technique for utilizing a biopolymer originated from insects. The inventors have taken note of the facts that the microsporidian spores can be produced in the insect's bodies or cultured cells in a high efficiency and each of the resulting microsporidian spores thus produced has the uniform particle size and has a shape of a sphere or an elliptical sphere and that the major cell wall substance of the microsporidian spores is chitin; have found out, for the first time, that if a substance such as an antibiotic or a physiologically active substance is immobilized on the chitin beads or chitosan beads having the uniform particle size, the beads can be used as carriers for sustained release of these substances; and thus have completed the present invention.

When inoculating microsporidian spores into or on domesticated silkworms, wild silkworms or other various insects or cultured cells, there are proliferated a large amount of microsporidian spores whose principal cell wall substance is chitin and having the particle size on the order of several micrometers ($\mu$m). The inventors of this invention have also developed a method for purifying/separating the proliferated microsporidian spores thus obtained to give chitin beads, chitosan beads or microsporidian spores each having the uniform particle size and a simple method for preparing carriers, from these beads, for the immobilization of, for instance, an antibiotic or a physiologically active substance.

First of all, the inventors of this invention have clarified optimum conditions for efficiently producing microsporidian spores, such as the time or the stage of an insect to inoculate microsporidian spores into or on insects or cultured cells, the amount thereof to be inoculated and the method for inoculating the same, as well as methods for purifying and/or separating the microsporidian spores proliferated, for instance, in the insect's bodies.

As methods for inoculating microsporidian spores into insects or cultured cells, there have been known, for instance, (i) an oral inoculation method which comprises the step of adding intended microsporidian spores to feeds for insects; and (ii) a direct inoculation method which comprises the step of percutaneously inoculating microsporidian spores into insect's bodies during breeding the same.

Although microsporidian spores may have a variety of shapes, they maintain desired bead shapes depending on the kinds thereof and the major cell wall substance is a complex of chitin and proteins. Thus, these spores may be used in the form of (i) chitin beads, i.e., microsporidian spores per se obtained after the proliferation or (ii) chitosan beads obtained by N-deacetylating the chitin of the microsporidian spores. Alternatively, chitosan beads in which the fine particle's surface is composed of chitosan may likewise be prepared by subjecting the chitin on the surface of microsporidian spores to an N-deacetylation treatment. Moreover, it is also possible to prepare hollow beads which have fine pores formed on the cell walls of the microsporidian spores by activating intracellular substances to thus outwardly release the same through the cell walls.

As has been discussed above, the chitin beads according to the present invention are those having the uniform and fine particle size, composed of microsporidian spores proliferated in insect's bodies or cultured cells and whose major cell wall substance is chitin, while the chitosan beads according to the present invention are the foregoing chitin beads wherein the chitin among the cell wall substances is subjected to N-deacetylation. These chitin beads and chitosan beads may be those from which the proteins have been removed, i.e., non-antigenic ones. The removal of the proteins is carried out by the usual hydrolysis treatment. In addition, the foregoing proliferated microsporidian spores may, if necessary, have pores in their cell walls and the foregoing chitin beads and chitosan beads may be hollow beads. The pores may be formed through a treatment of the beads with hydrogen peroxide or an alkali.

The carrier according to the present invention comprises chitin beads having the uniform and fine particle size which are composed of the aforementioned proliferated microsporidian spores and whose principal cell wall substance is chitin or chitosan beads wherein the chitin as the major cell wall substance is subjected to an N-deacetylation treatment. These chitin beads and chitosan beads may be those from which the proteins have been removed, i.e., non-antigenic ones. The removal of the proteins is carried out by the usual hydrolysis treatment. The foregoing proliferated microsporidian spores may, if necessary, have pores in their cell walls and the foregoing chitin beads and chitosan beads may be hollow beads. The pores may be formed through a treatment of the beads with an alkali or hydroxy peroxide.

The carrier according to the present invention is used for the immobilization or introduction of, for instance, physiologically active substances, antibiotics, biological cells, microorganisms such as bacteria, colorless and colored dyes, medicines, agricultural agents, perfumes, foodstuffs and feedstuffs.

Incidentally, the chitin beads and the chitosan beads according to the present invention are desirably non-antigenic ones when embedding them in, for instance, human bodies.

The method for preparing the uniform and fine particles (the chitin beads and the chitosan beads) according to the present invention comprises the steps of orally or percutaneously inoculating microsporidian spores in a concentration of $5\times10^2$ to $5\times10^8$ spores/ml, preferably $5\times10^2$ to $5\times10^7$ spores/ml, into an insect's body to thus proliferate the microsporidian spores, harvesting the proliferated microsporidian spores from the raised or grown insect's body, purifying the spores to thus give uniform and fine particles (chitin beads) and, if necessary, N-deacetylating the chitin of the chitin beads to give uniform and fine particulate chitosan beads. In this regard, if the spore concentration is less than $5\times10^2$ spores/ml, the rate of infection of the insect with the spores is low and there is observed a scattering in the rate of infection, while if it exceeds $5\times10^8$ spores/ml, the insect is killed prior to the complete formation of spores within the insect's body and therefore, the use thereof in such a concentration is unfavorable in view of profits. Preferably, the time for inoculating microsporozoa in the insect's body is just after the 2nd instar larva and the collection of the spores is started from the 5th instar larva. The insect is preferably larvae of domesticated silkworms.

The method for producing microsporidian spores according to the present invention preferably comprises the steps of adding cultured cells originated from an insect to a cell culture medium containing, on the basis of the weight of the cell culture medium, 5 to 50% by weight and preferably 10 to 40% by weight of the supernatant of hemolymphor or humor of larvae of domesticated silkworms, inoculating microsporidian spores into the culture medium to thus proliferate the cells and then recovering the microsporidian spores from the proliferated cells. In this respect, if the added amount of the supernatant of the hemolymphor of larvae of domesticated silkworms is less than 5% by weight and it exceeds 50% by weight, the spores scarcely undergo any proliferation. In addition, the spores would further efficiently be proliferated if the amount of the supernatant to be added falls within the preferred range defined above.

BEST MODE FOR CARRYING OUT THE INVENTION

Figure 1:
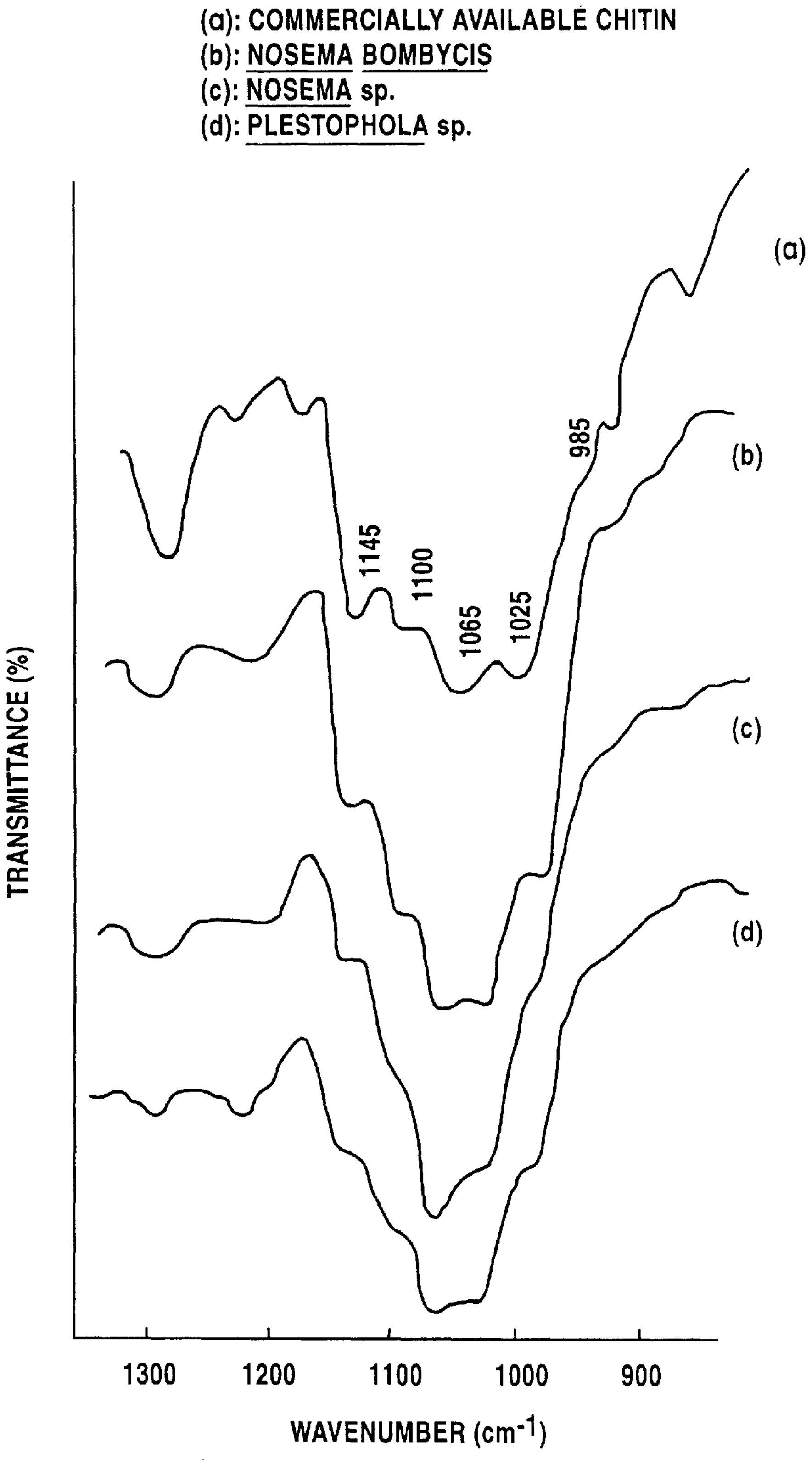
FIG. 1 shows an infrared absorption spectrogram of the dry powder (chitin beads) as prepared in Example 2, which is compared with that observed for chitin as a standard sample.

The microsporozoa used in the present invention are not particularly restricted to any specific one inasmuch as they have spores which are in a certain bead-like shape and whose major cell wall substance is chitin. Specific examples thereof usable in the present invention include microsporidian organisms belonging to the genus Nosema such as *Nosema bombycis, Nosema bombycis* (No. 402), *Nosema bombycis* (No. 408), *Nosema bombycis* (No. 520), *Nosema bombycis* (No. 611) and Nosema sp. (M 11), Nosema sp. (M 14); Vairimorpha (M 12), Plestophola (M 25), Plestophola (M 27) and Thelophania sp.

Hosts for proliferating microsporidian spores which can be used in the present invention include a wide variety of insects such as domesticated silkworms, large cabbage butterfly (*Pieris brassicae*), *Hyphantria cunea, Aporia crataegi, Spilosoma subcarnea* Walker, *Philosamia cynthia arrinda, Philosamia cynthia* or the like. Among these insects, particularly desirable are domesticated silkworms in which the method for breeding and the techniques for breeding have been well-established and which have synthetically studied from all of the views, i.e., genetic, thremmatological, physiological and ecological side views. The use of the larvae of domesticated silkworms would permit the production of a large amount of the microsporidian spores. In order to produce the microsporidian spores while using domesticated silkworms as hosts, it is preferred that microsporidian spores be orally or percutaneously inoculated into their 2nd instar larvae in the amount ranging from $5\times10^2$ to $5\times10^7$ spores/ml per silkworm and that a large amount of microsporidian spores proliferated till their 5th instar larvae be isolated and purified. This is because if microsporidian spores are orally inoculated into the 1st instar domesticated silkworm larvae, the silkworms inoculated therewith would be killed before the formation of microsporidian spores. On the other hand, if the protozoa of *Nosema bombycis* per se are administered to domesticated silkworms, it would be most efficient that the spores are inoculated into each silkworm (the 2nd instar larva) in such a manner that the intake per silkworm is equal to $5\times10^2$ to $3\times10^3$ spores and that the microsporidian spores are harvested from the larva bodies after about 12 days from the inoculation. At this stage, the larvae begin to die.

As has been discussed above, the present invention permits the harvest of a large amount of desired microsporidian spores in the insect's bodies or cultured cells. In this regard, the hosts may be insects such as domesticated silkworms or the spores may likewise be produced using cultured cells derived from mammals, and wide variety of other vertebrates and invertebrates. The insects after the inoculation of the spores may be raised according to the usual method at temperatures ranging from 15 to 32° C. and preferably 25 to 28° C. On the other hand, the cultured cells after the inoculation of the spores are desirably incubated at temperatures ranging from 20 to 30° C. and preferably 25 to 28° C.

Examples of cultured cells which can be used in the present invention are as follows:

Examples of cultured cells derived from domesticated silkworms are *Bombyx mori* S.P.C. Bm36, *Bombyx mori* Bm N-4 and *Bombyx mori* SES-BoMo-15A; examples of those derived from *Antheraea pernyi* include *Antheraea pernyi* NIS ES-AnPe-428; and examples of those derived from *Philosamia cynthia* include *Philosamia cynthia pernyi* NIS ES-SaCy-12. Moreover, examples of cultured cells derived from *Spilosoma imparilis* Butler include *Spilosoma imparilis* FRI-SpIm-1229; and examples of those derived from *Mamestra brassicae* include *Mamestra brassicae* SES-MaBr-4.

Among the foregoing cultured cells, *Antheraea pernyi* NIS ES-AnPe-428 permits the highly efficient proliferation of microsporidian spores in the cultured cell bodies at incubation temperatures ranging from 20 to 30° C., preferably 25 to 28° C. when using the Grace culture medium containing 5 to 50% of the supernatant of the hemolymphor from domesticated silkworm's larvae. The cultured cells other than *Antheraea pernyi* NIS ES-AnPe-428 may be incubated in a liquid culture medium commonly used in this field (YOKOTA et al., Kyushu Sanshi, 1995, 34).

When incubating these spores using cultured cells, the addition of the supernatant of the domesticated silkworm's hemolymphor to the culture medium in a predetermined concentration permits easy proliferation of the microsporidian spores within the cultured cells and the formation of a large amount of the spores. The amount of the supernatant of the domesticated silkworm's hemolymphor to be added to the culture medium in order to economically and efficiently produce the microsporidian spores preferably ranges from 10 to 40% by weight on the basis of the amount of the culture medium. The incubation conditions may be the same as those used when any supernatant is not added to the culture medium. A simple and effective method for collecting the hemolymphor may comprise the steps of cutting the legs of the 5th instar domesticated silkworm larvae with scissors and collecting the hemolymphor in a glass test tube which is ice-cooled. It is preferred that the hemolymphor thus collected be heated at 60° C. for 15 minutes in a water bath to thus precipitate out the proteins included in the hemolymphor, followed by removal of the proteins through the decantation to thus give a supernatant of the hemolymphor of domesticated silkworms which is ready for practical use.

The use of cultured cells derived from insects permits the simple and efficient production of microsporidian spores by the tank-incubation without any restriction in, for instance, the breeding and collection of insects and the procurement of the same.

When administering the microsporidian spores to *Antheraea eucalypti* cells which are cultured cells derived from wild type silkworms, it is efficient to produce microsporidian spores in cultured cell bodies according to a method comprising directly inoculating microsporidian spores in cells present in a commercially available cell culture medium (for instance, Grace culture medium available from Gibco Company) to which the supernatant of the domesticated silkworm's hemolymphor is added in an amount of at highest 40%.

The spores produced by insects or cultured cells derived from insects which are inoculated with the microsporidian spores have strong ability of infecting the domesticated silkworms and therefore, the spores thus collected are desirably detoxicated by treating them with formalin or an alcohol or by applying heat thereto, in order to prevent any contamination of domesticated silkworms with the spores. The microsporidian spores per se obtained after the detoxication thereof can be used as chitin fine particles (chitin beads) which are insoluble in water.

The purification of the proliferated microsporidian spores when producing the chitin beads having the uniform and fine particle size according to the present invention may be carried out as follows. The insect's larvae, within the bodies of which microsporidian spores are proliferated, are pulverized in, for instance, a 0.85% sodium chloride aqueous solution, followed by filtering the aqueous dispersion through an absorbent cotton layer, to thus collect spores and then repeating twice centrifugation using a centrifugal separator, then loading the spores on a layer of Percoll (trade name) which is available from Pharmacia Company of Sweden and centrifugation at 3,000 rpm for 30 minutes to thus purify the microsporidian spores.

The N-deacetylation treatment for converting chitin into chitosan may be carried out according to the usual method which comprises, for instance, the steps of treating chitin beads of the microsporidian spores in a 30 to 50% sodium hydroxide aqueous solution at temperatures ranging from 80 to 120° C. for several hours to deacetylate chitin as a cell wall substance and to thus convert the chitin beads into chitosan beads. In this method, there may be used conventionally known reagents and conditions for the N-deacetylation such as pH (Brine et al., Comp. Biochem. Physiol., 1983, 69B, p. 283).

The cell wall substances of the chitin beads and the chitosan beads according to the present invention are constituted by non-antigenic chitin, chitosan and glucan as well as antigenic proteins. The proteins may be hydrolyzed with an acid and/or an alkali to thus dissolve out and remove the same, but the beads do not undergo any change in their shape during the treatment. The hydrolysis treatment is carried out at temperatures ranging from 5 to 35° C. for 1 to 25 hours, preferably 20 to 25° C. for 8 to 15 hours and more preferably at room temperature for 10 to 12 hours using a 0.1 to 3N, preferably 0.5 to 2N and more preferably 0.9 to 1.3N aqueous solution of sodium hydroxide or hydrogen chloride to thus give non-antigenic beads. The hydrolysis treatment may be carried out first with an acidic aqueous solution and then with an alkali aqueous solution; or the treatment may be carried out first with an aqueous alkaline solution and then with an aqueous acid solution. It is desirable to repeat a cycle over at least several times (preferably over 5 times), wherein each cycle comprises an acid treatment and an alkali treatment. Finally, the resulting spores are washed with water and then washed with ethanol in a concentration of not less than 95% by weight for a prescribed time to sterilize and dehydrate the spores. Thus, the proteins as the cell wall substances of the microsporidian spores can completely be eliminated.

To immobilize, on the microsporidian spores, or introduce, into the spores, antibiotics, bacteria, physiologically active substances, medicines and living cells, it would be effective to form fine pores on or through the cell walls of the microsporidian spores. These fine pores may be formed in the microsporidian spores according to any method which is not particularly restricted, but preferred are the following two methods:

(i) A method which comprises the step of mixing equal amounts of a 1 to 6% by weight $H_2O_2$ solution and a spore suspension; and (ii) A method comprising the steps of immersing microsporidian spores in a 0.2N KOH solution maintained at 25° C. for 30 minutes and then adjusting the pH value of the immersion solution to a neutral level by addition of a phosphate buffer having a pH of 7.2 in small portions.

If the cellular substances in the spores are activated by treating the microsporidian spores with an aqueous alkali solution, the intracellular substances are outwardly released from the spore to thus form fine pores, on or through the spore wall, having a diameter on the order of, for instance, about 0.1 to 0.3 μm depending on the size of the spores and accordingly, the fine pores thus formed on or through the wall of the microsporidian spores may be utilized. More specifically, the microsporidian spores are first treated at temperatures ranging from 15 to 20° C. for 30 minutes using a 0.2N aqueous solution of potassium hydroxide, then neutralized with a phosphate buffer having a pH of 7.2 to activate the cellular substances present in the spores. Thus, fine pores are formed when the intracellular substances present in the spores are released into the culture medium used for the incubation of the insect's cultured cells.

The microsporidian spores per se after the proliferation serve as antigens, but the chitin beads and the chitosan beads from which the cell wall substances, i.e. proteins, have been removed through the acid and/or alkaline hydrolysis do not have a function as an antigen, as has been discussed above.

As has been described above, the present invention permits the production of chitin beads having a spherical shape or an elliptic-spherical shape, having the size on the order of about several micrometers (μm) and the uniform and fine particle size as well as the production of chitosan beads by N-deacetylation of the chitin beads, if using microsporidian spores capable of being considerably proliferated in insect's bodies or cultured cells. In addition, the present invention also permits the production of beads having the uniform and fine particle size, which cannot easily be prepared according to the conventional methods, in particular, beads having the particle size on the order of about 1 to 6 μm and free of any scattering in particle size, as well as hollow chitosan beads. The chitin beads and the chitosan beads having the uniform and fine particle size and prepared according to such a method may be used as carriers for drug-delivery systems and materials for cosmetic foundations. The present invention allows the production of these chitin beads and chitosan beads having a variety of sizes depending on the kinds of the microsporozoon used. Moreover, if enzymes or living cells are adhered to or immobilized on the chitosan beads, the beads may be used to constitute a bioreactor effective in food industries and other various industrial fields.

The chitin beads and the chitosan beads according to the present invention comprise highly reactive chemical components and therefore, an enzyme or an immunological antibody may be chemically or physically linked to the surface of these beads. For instance, if immobilizing antigen/antibody such as immunoglobulin on the particle surface and/or the interior of the particles, the resulting product can be used as an immunological carrier. Moreover, modified chitin beads which is modified by converting the chitin moiety thereof into glycol chitin and carboxymethyl chitin through a chemical reaction are excellent in moisture retention properties and therefore, can be used as a material for cosmetics. Moreover, if a vinyl compound or the like is grafted on the microsporidian spore or the chitin beads and then an enzyme such as α-amylase is immobilized on the grafted chitin beads, the beads not only permit the improvement in the stability of the enzyme activity, but also permit the exhibition of still further efficient enzyme activity while making the most use of characteristic properties of the fine particles, i.e., a very large effective surface area.

In case of the chitin beads and the chitosan beads originated from insects, the cell wall substances of these beads obtained after the hydrolysis treatment are composed of, for instance, chitin, chitosan and glucan which are all components hardly serving as antigens, as has been discussed above. For this reason, these chitin beads and the chitosan beads are free of any antigen/antibody reaction even when embedding them in animal bodies including human bodies as sustained release carriers. This is because the microsporidian spores from which proteins among the cell wall substances are removed lose their antigenicity. Moreover, the chitin beads and the chitosan beads would be decomposed by the action of the enzymes present in the bodies after a certain time period and therefore, can be used as safe materials capable of being decomposed in living bodies.

The chitin beads and the chitosan beads according to the present invention may be hollow beads which comprise vacant space therein and in this case, fine pores are formed on and/or through the cell wall tissue. Accordingly, living cells, bacteria, antibiotics, biologically active substances or the like may be introduced into these fine pores in an environment maintained at a reduced pressure. When microorganisms such as bacteria are encapsulated into the beads, the microorganisms encapsulated therein are not easily affected by external factors capable of modifying proteins such as ultraviolet light rays and thus these beads can be used as materials for protecting the natural enemy microorganisms from the action of such external factors.

The chitin beads and the chitosan beads according to the present invention may be used as, for instance, supports for the affinity chromatography, carriers for cell culture and auxiliary agents for medicines and show excellent characteristic properties as base materials for encapsulation, into microcapsules, of drugs, biologically active substances, hormones, vaccines or the like. Microcapsules in which, for instance, agricultural chemicals or fertilizers are encapsulated into the microsporidian spores, the chitin beads or the chitosan beads may be used as soil conditioners and those obtained by encapsulating feed components or foodstuffs, which show their efficacy in an extremely small amount or a trace amount, in the chitin beads or the chitosan beads may be used as feeds for domestic animals or those for pisciculture. In addition, the microsporidian spores, the chitin beads or the chitosan beads in which bacteria or the like are encapsulated or on which they are immobilized have an effect of protecting these bacteria or the like from the irradiation with ultraviolet light rays and accordingly, they can be used as materials for protecting organisms. In particular, if the chitin beads and the chitosan beads have a uniform particle size, they can be used in special applications in the fields of, for instance, fine chemicals. Moreover, when applying the microcapsules comprising the chitin and chitosan components according to the present invention to pressure-sensitive copying paper, they can improve the drying characteristics of the paper during smearing processes and also permit considerable improvement of the color developing and printing characteristics of the copying paper.

Thus, the chitin and chitosan fine particles may effectively be used in wide variety of fields such as agriculture, industries, medical science and food.

As has been discussed above, when irradiating, with ultraviolet light rays, microsporidian spores, the chitin beads and chitosan beads in which microorganisms such as bacteria, physiologically active substances or the like are encapsulated, the chitin and chitosan as the major cell wall substances can block the energy of ultraviolet rays through absorption of the ultraviolet rays. Accordingly, they can hold the biological and physiological activities of, for instance, the microorganisms such as bacteria and physiologically active substances, which are encapsulated in the microsporidian spores, the chitin beads and chitosan beads, over a long time period. Thus, the microsporidian spores, the chitin beads and chitosan beads are effective for inhibiting any reduction, in activity, of microorganisms such as bacteria and physiologically active substances encapsulated therein.

The chitin beads and the chitosan beads according to the present invention from which proteins have been removed hardly serve as antigens even when they are embedded in living tissues and do not adversely affect the living body. Therefore, any problem on the basis of an antigen/antibody reaction does not arise at all even if a medicine or the like having physiological activity is immobilized on the beads and the resulting beads are embedded in living bodies such as human bodies. For this reason, the chitin beads and the chitosan beads in which a medicine, in particular, showing an anti-cancer effect is encapsulated may be used in a frontier medical field as missile carrier for treating specific lesions.

Moreover, these beads permit the easy control of the sustained release rate, the sustained release amount and the degree of biodegradation of, for instance, medicines, physiologically active substances and antibiotics which are supported by or encapsulated in the beads, by properly adjusting the degree of the hydrolysis, or by controlling the degree of fine pores formed by activating the cellular substances in the microsporidian spores so that the spores thus extracellularly discharge their contents.

EXAMPLES

Then the present invention will hereunder be described in more detail with reference to the following working Examples and Comparative Examples, but the present invention is by no means limited to these specific Examples. Incidentally, there have been known various species of microsporozoa, but *Nosema bombycis* species originated from larvae of domesticated silkworms were used in the following Examples and Comparative Examples, unless otherwise specified.

In the following Examples and Comparative Examples, the bacterial activity and the antigenicity were evaluated according to the following methods.

A. Evaluation of Bacterial Activity

Semisynthetic Wakimoto Culture Medium or King B Culture Medium (15 ml) which had been dissolved with heating and then maintained at 55° C. was admixed with 2 ml of a liquid containing the spores of bacteria to be inspected (concentration: $10^9$ to $10^{10}$ spores/ml) and then the resulting mixture was poured into a petri dish to thus solidify the same in a plate-like shape. A test sample (10 μl) was dropwise added to this bacteria liquid-mixed plate culture medium, followed by maintaining the temperature thereof at 20 to 25° C. for 2 days, and then evaluation of the degree of inhibition of the bacterial proliferation in the culture medium present just under the test sample according to the following 5 stage criteria:

+++: Strong Inhibition (the bacteria did not proliferate at all and the transparency of the culture medium was high like transparent glass);

++: Slightly Strong Inhibition;

+: Weak Inhibition (the bacteria underwent slight proliferation and the transparency of the culture medium lay between the transparent glass and the frosted glass);

±: Slight Inhibition (the proliferation of the bacteria was about ⅕ and the transparency of the culture medium corresponded to that of the frosted glass);

−: the bacteria was sufficiently proliferated and the culture medium was opaque.

B. Method for Inspecting Beads for Antibacterial Activity to Mold Fungi

PSA Culture Medium which had been dissolved with heating and then maintained at 55° C. was admixed with 2 ml of a liquid containing the spores of mold fungi be inspected (concentration: $10^5$ to $10^6$ spores/ml) and then the resulting mixture was poured into a petri dish to thus solidify the same in a plate-like shape, followed by the same procedures and observation as used in the foregoing evaluation of bacterial activity.

C. Evaluation of Antigenicity

An antiserum for microsporidian spores was prepared as follows. Spores which had been grown successively using larvae of domesticated silkworms were purified according to the Percoll density gradient centrifugation, subjected to centrifugation at 2,000 rpm for 10 minutes, followed by suspending the precipitated spores in a 0.85% NaCl solution to give a spore suspension ($2\times10^8$ spores/ml) to be used as an antigen, mixing the suspension with an equal amount of Freund's complete adjuvant and intramuscularly injecting 2.0 ml of the resulting mixture once into each rabbit. Thereafter, 1 ml of each of the spore suspension was intravenously injected 4 times into each rabbit in intervals of one week and the blood was collected after 7 days from the final injection. The serum was inactivated at 56° C. for 30 minutes and stored at −20° C.

The antigen for agglutination reaction was prepared by treating the purified microsporidian spores with 1% formaldehyde, then washing with distilled water through centrifugation and suspending the spores in a 0.85% NaCl solution ($4\times10^7$ spores/ml).

The foregoing antiserum was diluted with a 0.85% NaCl solution according to the two-fold serial dilution method, then mixed with an equal amount of the spore suspension on a slide glass, followed by reacting them at 37° C. for one hour and observation through an inverted microscope to thus determine the agglutinin titer. The dilution ratio of the antibody (antiserum) was set at 16, 32, 64, 128, 256, 512, 1024 and 2040 and the evaluation was carried out according to the following two-stage criteria:

+: There was observed an antigen/antibody reaction;

−: There was not observed any antigen/antibody reaction at all.

Example 1

A variety of microsporidian spores were inoculated into larvae of domesticated silkworms, followed by incubating the same to thus examine the name of species of various kinds of microsporidian spores which could be separated from the larvae of domesticated silkworms, the size of the spores and the antigenicity thereof. As microsporozoa, there were used, as shown in Table 1, *Nosema bombycis* (standard species used for the comparison of characteristic properties with those of other microsporozoa), *Nosema bombycis* (No. 402), *Nosema bombycis* (No. 408), *Nosema bombycis* (No. 520), *Nosema bombycis* (No. 611), Nosema sp. (M 11), Vairimorpha (M 12), Nosema sp. (M 14), Plestophola (M 25), Plestophola (M 27) and Thelophania sp. The results obtained by the investigation are listed in the following Table 1.

The microsporidian spores used generally had elliptic shapes wherein the major and minor axes of the ellipse were 3 to 5 μm and 1 to 3 μm, respectively and it was found that the shape and size of the microsporidian spores were almost determined by the kind of the corresponding microsporozoon. More specifically, the present invention permits arbitrary production of chitin beads and chitosan beads having uniform shapes by appropriately selecting each particular kind of microsporozoon. The major axes of various kinds of microsporidian spores are at longest about 5 μm and accordingly, microsporozoon adapted for a desired applications may be selected and used. In addition, the parasitic sites on silkworms are also listed in Table 1.

TABLE 1

| Microsporozoon | Generic Name | Size of Spore (μm) | Parasitic Site |
|---|---|---|---|
| *Nosema bombycis** | Nosema | 3.8 × 2.2 | whole body |
| *Nosema bombycis* (No. 402) | Nosema | 3.9 × 2.0 | whole body |
| *Nosema bombycis* (No. 408) | Nosema | 3.8 × 2.1 | whole body |
| *Nosema bombycis* (No. 520) | Nosema | 3.7 × 2.2 | whole body |
| *Nosema bombycis* (No. 611) | Nosema | 4.1 × 2.1 | whole body |
| Nosema sp. (M 11) | Nosema | 3.9 × 1.7 | whole body |
| Vairimorpha (M 12) | Vairimorpha | 5.1 × 2.0 | whole body |
| Nosema sp. (M 14) | Nosema | 4.2 × 2.4 | whole body |
| Plestophola (M 25) | Plestophola | 4.9 × 2.8 | whole body |
| Plestophola (M 27) | Plestophola | 2.5 × 1.3 | mid-gut |
| Thelophania sp. | Thelophania | 3.4 × 1.7 | whole body |

Note)
*: Standard Species

The above-mentioned Nosema bombycis* (Nosema bombycis Nageli as standard species), Nosema sp. (M 11) and Vairimorpha (M 12) are stored in National Institute of Sericultural and Entomological Science Ministry of Agriculture, Forestry and Fisheries under Registration Nos. 860001, 860004 and 860005, respectively, and could be obtained from the Institute by a person skilled in the art at the time of the priority date of this application.

In addition, these microsporozoa have been deposited with American Type Culture Collection (ATCC), 10801, University Boulevard, Manassas, Va. 20110-2209, U.S.A., under the Budapest Treaty on Mar. 23, 1998, the designations to the deposits being Nosema bombycis Nageli: 209694, Nosema sp. M 11:209693, and Vairimorpha M 12:209692, respectively. The microsporozoa thus deposited can be obtained from ATCC by a third party.

Example 2

Using microsporozoan protozoa of *Nosema bombycis,* Nosema sp. (M 11) and Plestophola sp. as disclosed in the foregoing Table 1, microsporidian spores ($3\times10^3$ spores/ml, each) of each protozoan were orally inoculated into each of the 2nd instar domesticated silkworm larvae (Nichi (Japan) No. 135 X Shi (China) No. 135), followed by proliferation of the microsporidian spores within the silkworm bodies, taking the resulting spores out of the silkworm bodies, lyophilizing them at −30° C. and then drying them in a lyophilizing machine available from Tozai Tsusho K.K. to give dry powder. In order to briefly and qualitatively inspect the dry powder obtained from the spore-containing liquid for chemical components thereof, the dry powder sample was admixed with lithium bromide, converted into a pellet or tablet, followed by inspection thereof for the infrared absorption spectra within the wave-number range of from 900 to 1200 $cm^{-1}$ using an infrared spectrometer available from Nippon Bunko Kogyo K.K. In this regard, chitin available from Wako Pure Chemical Co., Ltd. was used as the standard or control sample. The results thus obtained are plotted on FIG. 1. In FIG. 1, the commercially available chitin shows the IR absorption spectral curve a and chitin products derived from *Nosema bombycis,* Nosema sp. and Plestophola sp. as the microsporozoan protozoa show the IR absorption spectral curves b, c and d respectively. In the IR absorption spectral chart of the resulting chitin standard sample, absorption bands were observed at wavenumbers of 985, 1025, 1065, 1100 and 1145 $cm^{-1}$. There were observed approximately identical absorption bands within almost the same wavenumber region (1000 to 1200 $cm^{-1}$) observed for the chitin standard sample irrespective of the kinds of the microsporozoan protozoa. This clearly indicates that chitin is a major component which constitutes the cell wall of the various kinds of microsporidian spores.

Moreover, the same results as observed above could be obtained even when percutaneous inoculation was substituted for the oral inoculation.

In addition, microsporidian spores whose cell wall is mainly composed of chitin like the foregoing spores can be obtained when using, as hosts for microsporidian spores, large cabbage butterfly (*Pieris brassicae*), *Hyphantria cunea, Aporia crataegi, Spilosoma subcarnea* Walker, *Philosamia cynthia arrinda, Philosamia cynthia* or the like in place of domesticated silkworms.

Example 3

To qualitatively analyze crystalline forms of dried spore powder obtained from the same microsporozoan protozoa as used in Example 2, X-ray diffraction patterns were obtained using an X-ray diffractometer (available from Rigaku Denki K.K.). The measured interplanar spacings of the resulting samples are listed in the following Table 2 together with those observed for the standard chitin sample. All of the X-ray diffraction patterns of these samples showed diffraction patterns corresponding to the interplanar spacings of 8.53, 6.70, 4.64 and 3.31 Å, but they were all accompanied by wide halation. On the other hand, in the X-ray diffraction pattern observed for the chitin standard sample, there were detected X-ray diffraction corresponding to the interplanar spacings of 9.30, 6.90, 4.64, 3.36, 3.00 and 2.80 Å and this was similar to the X-ray diffraction patterns observed for the spores. Thus, it is also confirmed that the major substance constituting the cell walls of the microsporidian spores is chitin.

TABLE 2

| Interference Ring | Standard Chitin | *Nosema bombycis** | Nosema sp.(Ae) | Plestophola sp. |
|---|---|---|---|---|
| $R_1$ | 9.30(vs) | 8.53(w) | 8.70(w) | 8.70 |
| $R_2$ | 6.90(m) | 6.70 | 6.7(w) | 6.70 |
| $R_3$ | 4.64(vs) | 3.31 | 4.61 (s) | 4.61(m) |
| $R_4$ | 3.36(s) | 3.31 | 3.39 | 3.31(m) |

TABLE 2-continued

| Interference Ring | Standard Chitin | *Nosema bombycis** | Nosema sp.(Ae) | Plestophola sp. |
|---|---|---|---|---|
| $R_5$ | 3.00(w) | — | — | — |
| $R_6$ | 2.80(vw) | — | — | — |

Example 4

The spores derived from the Microsporozoon, *Nosema bombycis* stored in National Institute of Sericultural and Entomological Science Ministry of Agriculture, Forestry and Fisheries were used as the spore sample, the microsporidian spores ($3\times10^3$ spores/ml) were orally inoculated into each of the 2nd instar domesticated silkworm larvae (Nichi (Japan) No. 135 X Shi (China) No. 135). A very large amount of the microsporidian spores were proliferated within the larva bodies of the domesticated silkworm, this resulted in sporulation and accordingly, all of the larvae of domesticated silkworms suffered from the microsporidiosis and died from the disease at the 5th instar. The killed larvae were pulverized in a 0.85% sodium chloride aqueous solution and then filtered through an absorbent wadding layer to collect the resulting spores. The purification of the spores was carried out by loading 2 parts of a suspension of the spores in a 0.85% sodium chloride aqueous solution on 8 parts of Percoll (trade name; available from Pharmacia of Sweden) and then subjecting it to centrifugation at 3,000 rpm and 20° C. for 30 minutes.

The number of *Nosema bombycis* spores collected from one larva of domesticated silkworm was found to be about $1\times10^{10}$ in all. The aqueous suspension of the spores was dried to give 100 mg of powdery spores.

The above-mentioned *Nosema bombycis* could be obtained, from The National Institute of Sericultural and Entomological Science Ministry of Agriculture, Forestry and Fisheries, by a person skilled in the art at the time of the filing date of this application.

Example 5

The sporulation of Microsporozoon, *Nosema bombycis,* in *Antheraea eucalypti* cultured cells was investigated as follows. Cultured cells of *Antheraea eucalypti* were inoculated into commercially available cell culture mediums (Grace culture medium available from Gibco Company) to which different amounts of the serum of domesticated silkworms (the supernatant of the hemolymphor derived from domesticated silkworms) were added, followed by addition of a constant amount of the pores of Microsporozoon (*Nosema bombycis*) thereto, incubation thereof for a predetermined time period and determination of the number of spores included in a unit volume of the culture medium (1 ml) using a hemocytometer through microscopic observation. The legs of the 5th instar domesticated silkworm larvae were cut with scissors, followed by collecting the hemolymphor in a glass test tube which was ice-cooled, heating the collected hemolymphor at 60° C. for 15 minutes in a water bath to thus remove the proteins included in the hemolymphor and thus give a supernatant of the hemolymphor which was used in this Example 5. The results of the measurements are listed in the following Table 3.

As will be seen from the results, if the supernatant of the domesticated silkworm's hemolymphor is added to the culture medium in a predetermined concentration upon proliferation of cultured cells, the microsporidian spores are easily and considerably proliferated within the cultured cells to thus form a large amount of spores. The amount of the supernatant of the domesticated silkworm's hemolymphor to be added for economical and efficient production of the microsporidian spores is in general ranges from about 5 to 50% by weight and preferably about 10 to 40% by weight on the basis of the weight of the culture medium.

TABLE 3

| Added Amount of Hemolymphor Supernatant (wt %) | Number of Spores/ml |
|---|---|
| 0 | 0.07 |
| 5 | 0.37 |
| 10 | 1.92 |
| 20 | 3.24 |
| 30 | 3.24 |
| 40 | 2.18 |
| 50 | 0.86 |

Example 6

Proliferation of microsporidian spores within the cultured cells was investigated using cultured cells derived from insects other than those used in Example 5. *Nosema bombycis* and Nosema sp. (M 11) were inoculated into different kinds of insect's cultured cells to thus examine any increase in the number of microsporidian spores proliferated in the insect's cultured cells. In this respect, the method for proliferating the cultured cells was the same as that used in Example 5 and the amount of the hemolymphor supernatant to be added to the culture medium was set at 0% and 20% on the basis of the weight of the cell culture medium. The results thus obtained are listed in Table 4.

TABLE 4

| Micro-sporidian Spore | Insect's Cultured cells | Number of spores/ml Concn. of Hemolymphor* 0% | 20% |
|---|---|---|---|
| *Nosema bombycis* | *Bombyx mori* SES-BoMo-15A | 2.28 | 6.94 |
| | *Antheraea pernyi* NIS ES-AnPe-428 | 0.09 | 0.56 |
| | *Philosamia cynthia* NIS ES-SaCy-12 | 0.04 | 0.88 |
| | *Spilosoma imparilis* is FRI-SpIm-1229 | 0.01 | 0.04 |
| | *Mamestra brassicae* SES-MaBr-4 | 0.01 | 0.04 |
| Nosema sp. (M 11) | *Bombyx mori* SES-BoMo-15A | 1.21 | 4.54 |
| | *Antheraea pernyi* NIS ES-AnPe-428 | 0.29 | 1.28 |
| | *Philosamia cynthia* NIS ES-SaCy-12 | 0.25 | 0.58 |
| | *Spilosoma imparilis* FRI-SpIm-1229 | 0.16 | 0.27 |
| | *Mamestra brassicae* SES-MaBr-4 | 0.12 | 0.64 |

Note)
*: Added amount of the domesticated silkworm's hemolymphor supernatant.

Example 7

Chitosan microspores were prepared from the cell wall substances of spores of microsporozoon, *Nosema bombycis**, prepared in the foregoing Example 4, according to the following method. First, the microsporidian spores were treated in a 40% sodium hydroxide solution at 80° C. for 4 hours, followed by addition of water to carry out washing. As a result, the chitin as the major component of the cell walls of the microspores was subjected to an N-deacetylation treatment. When each microsporidian spore was examined by an optical microscope and scanning electron microscope, it was confirmed that the microsporidian spore was not dissolved even when it was subjected to N-deacetylation and the shape of the microspore was also maintained.

Example 8

An antibiotic was adsorbed on the cell wall tissue of 2 mg of the powdery chitin spores which was *Nosema bombycis* spores treated by the same procedures as used in Example 4, whose content of the spore had been removed through hydrolysis, according to the following method. The foregoing hydrolysis was carried out by first treating with a 1N NaOH maintained at room temperature for 12 hours and then with a 1N HCl for 12 hours (these NaOH and HCl treatments constituted one cycle of hydrolysis). After repeating 5 cycles of hydrolysis in all, the spores were finally treated with 95% ethanol for 2 hours to dehydrate the same. Thus, the proteins as the cell wall substances of the microsporidian spores were completely removed from the spores. In addition, the adsorption of the antibiotics on the spores was carried out by introducing, into a tube, a solution of 10 mg of Rifampicin or Tetracycline dissolved in 3 ml of distilled water and the foregoing chitin spores, repeating three times pressure reduction-degassing cycle of the tube using a tap water-aspirator and further applying ultrasonics to the tube for 10 minutes so that the antibiotic could penetrate into the cell wall tissues. Then the tube was centrifuged at 2500 rpm for 20 minutes using a centrifuge to thus precipitate out chitin spores containing the antibiotic molecules. Furthermore, 10 ml of distilled water was added to the tube, followed by centrifugation, removal of the supernatant through decantation to thus isolate the chitin spores including Rifampicin or Tetracycline.

Whether Rifampicin or Tetracycline was supported on the *Nosema bombycis* spores or not was confirmed as follows. The *Nosema bombycis* spores obtained by thoroughly washing with water three times and then recovering through centrifugation at 3000 rpm for 20 minutes were inspected for the degree of inhibition of the proliferation of a causative bacterium of tomato bacterial canker (*Clavibactor michiganensis* pv. *michiganensis*). As a result, even the *Nosema bombycis* spores which had repeatedly been washed with water could completely inhibit any proliferation of the causative bacterium of tomato bacterial canker and thus it was judged that the antibiotic would be supported on the spores.

Example 9

A circular disk exclusively comprising *Nosema bombycis* spores was prepared as follows, while applying the method for preparing a sample disk for measuring IR absorption spectra as disclosed in Example 2, without using any lithium bromide:

The powdery *Nosema bombycis* spores (200 mg) obtained in Example 4 were introduced into a machine for forming tablet for use in IR absorption spectral measurement having a diameter of 10 mm ϕ available from Nippon Bunko Kogaku Kogyo K.K., followed by degassing for 20 minutes using a vacuum pump, application of a pressure of 150 $kg/cm^2$ to the tablet-forming machine using a hydraulic pressing apparatus, allowing to stand for 10 minutes at that pressure to thus give a tough circular disk having a thickness of about 0.3 mm. Thus, the microsporidian spores or the like prepared by the present invention may be used as bulk materials.

Example 10

The powdery *Nosema bombycis* spores (200 mg) produced in Example 4 were introduced into a 50 ml volume egg-plant type flask equipped with a condenser, followed by addition of 30 ml of a 40% by weight sodium hydroxide aqueous solution and then treating in an oil bath at a temperature of 100° C. for 3.0 hours to give chitosan beads having a degree of deacetylation of 93.6% and a uniform and fine particle size.

Example 11

Effect of Protecting Microorganisms as Natural Enemy (Effect of Protecting Bacteria from the Action of Ultraviolet Rays Using Microsporidian Spores)

Bacteria were encapsulated into microsporidian spores according to the following method. More specifically, there was introduced, into a centrifuge tube for cell culture, 2 mg of powdery *Nosema bombycis* spores which were prepared by removing the contents of the spores through hydrolysis performed under the same conditions as used in Example 8 and then treated in the same manner as used in Example 4, followed by addition of 2.0 ml of a suspension containing causative bacteria for the bacterial rot of an agaric (*Pseudomonas tolaasii*) or a causative bacterium of tomato bacterial canker (*Clavibactor michiganensis* pv. *michiganensis*) in a concentration of $10^9$ bacteria/ml, reducing the pressure in the tube using an aspirator which made use of tap water for 10 minutes and then introduction of air to release the reduced pressure. These procedures for reducing pressure and for introducing air were repeated three times. Then the tube was subjected to centrifugation using a centrifuge at 1000 rpm for 10 minutes to thus collect the spores on the bottom of the centrifuge tube. The precipitated spores (hereinafter referred to as "spore-containing section (S.C.S.)")(0.2 ml) were withdrawn from the tube and uniformly spread on an agar culture medium in a glass petri dish (a diameter of 9 cm) using an L-shaped rod. The spore-containing liquid was air-dried on the culture medium till the liquid lost its washy appearance, then the culture medium was positioned at 20 cm distant from the a UV lamp and irradiated with ultraviolet light rays for 10 seconds, 30 seconds, one minute, 2 minutes and 5 minutes. In this connection, the UV light rays-irradiation test was carried out in a clean bench and a germicidal lamp, National GL-15 (15 W), was used as a light source. After 3 days from the UV-irradiation, the number of bacteria appearing on a ⅙ surface area of the petri dish was counted to thus evaluate the effect of the microsporidian spores on the protection of the bacteria from the UV-irradiation. The results thus obtained are summarized in the following Table 5. Separately, a system completely free of the microsporidian spores was also precipitated by centrifugation in a centrifuge tube to thus determine the number of bacteria and this was used as a control (hereunder referred to as "spore-free section (S.F.S.)").

TABLE 5

Germicidal Lamp-Irradiation Time and Effect of Microsporidian Spores on Protection of Bacteria Encapsulated Therein

| UV | *Pseudomonas tolaasii*1) | | *Clavibactor michiganensis* pv. *michiganensis*2) | |
|---|---|---|---|---|
| (hr.) | S.F.S. | S.C.S | S.F.S. | S.C.S. |
| 0 sec | vast number | vast number | vast number | vast number |
| 10 sec | 91 | 89 | +++ | +++ |
| 30 sec | 16 | 81 | ++ | +++ |

TABLE 5-continued

Germicidal Lamp-Irradiation Time and Effect of Microsporidian Spores on Protection of Bacteria Encapsulated Therein

| UV | *Pseudomonas tolaasii*[1)] | | *Clavibactor michiganensis* pv. *michiganensis*[2)] | |
|---|---|---|---|---|
| (hr.) | S.F.S. | S.C.S | S.F.S. | S.C.S. |
| 1 min | 14 | 76 | + | +++ |
| 2 min | 11 | 50 | + | ++ |
| 5 min | 0 | 21 | − | ++ |

Note) :
[1)]causative bacteria for the bacterial rot of an agaric
[2)]causative bacteria for bacterial canker of tomato In Table 5, "vast number" means that the number of bacterial colonies appearing on the ⅙ area of the petri dish is too great to determine, while if the numbers of colonies are great, but can quantitatively be distinguished from one another, they are expressed according to the four stage evaluation extending from +++ to − (none).

The effect of the microsporidian spores on protection of bacteria from the action of UV-irradiation was quantitatively evaluated as follows. Using a semi-logarithmic graph paper, the logarithm of the number of bacteria appearing on the ⅙ area of the petri dish is plotted as the logarithmic axis and the irradiation time (unit: min) is plotted as abscissa. If determining the irradiation time required for reducing the number of bacteria appearing on the petri dish down to about 20 from the graph, it was found to be 30 seconds for the spore-free section and 5 minutes for the spore-containing section.

These results indicate that if the causative bacteria for the bacterial rot of an agaric were encapsulated in the *Nosema bombycis* spores, the rate of the killed bacteria among those encapsulated in the spores was low as compared with that observed for the spore-free group even when they were irradiated with UV light rays and the protection effect was approximately 10 times that for the spore-free group. Moreover, it is clear that, in case of the causative bacteria for bacterial canker of tomato, the encapsulation thereof in spores shows such a protection effect. This protection effect due to the encapsulation indicates that the microsporidian spores in which bacteria, enzymes, biologically active substances or the like are encapsulated are useful as, for instance, carriers for protecting natural enemy microorganisms.

Example 12

Test on Adsorption of Antibiotic on Chitin Spores

Chitin beads were modified into chitosan beads using an alkali solution having a high concentration according to the following method. Chitin beads (100 mg) was introduced into an egg-plant type flask equipped with a reflux condenser, followed by addition of 50 ml of a 30% by weight NaOH aqueous solution and a treatment thereof in an oil bath at 100° C. for 2 hours. After the completion of the reaction, the reaction system was washed with a sufficient amount of distilled water and then centrifuged by a centrifuge at 3000 rpm for 10 minutes to thus give chitosan beads. Then, to 0.2 ml of an aqueous solution of an antibiotic prepared by dissolving 10 mg of Rifampicin in 3 ml of water, there was added 0.5 mg of the foregoing chitosan beads, and then degassing was repeated 5 times with a tap water aspirator to give a fraction. The chitosan beads thus prepared was inspected for the effect of inhibiting the proliferation of the causative bacteria for bacterial canker of tomato, according to the same method as in Example 8, and it was confirmed that the chitosan beads fraction in which Rifampicin had been added and degassing had been repeated 5 times comprised the antibiotic adsorbed thereon. In order to examine whether or not the chitosan beads of microsporidian spores on which Rifampicin had been adsorbed were effective as sustained release supports or not, the sustained release effect thereof was evaluated using causative bacteria for bacterial canker of tomato.

As has been discussed above in detail, 0.5 mg of powdery chitosan beads of microsporidian spores were dispersed in 0.2 ml of the foregoing aqueous Rifampicin solution and the dispersion was introduced into a centrifuge tube. Then the dispersion was centrifuged at 5000 rpm for 3 minutes to thus separate precipitates of microsporidian spores from the supernatant. The precipitates (0.1 ml) was added to another centrifuge tube, followed by addition of 1 ml of fresh distilled water, again subjecting to centrifugation to thus separate precipitates of microsporidian spores from the supernatant according to the similar method. The precipitates and the supernatant thus obtained were inspected for the antibacterial effect on the proliferation of the causative bacteria for bacterial canker of tomato at predetermined intervals. The results thus obtained are summarized in the following Table 6.

TABLE 6

| Elapsed Time | Inhibitory Circle Radius (mm) | | |
|---|---|---|---|
| (day) | Precipitates | Supernatant | Diluted Supernatant |
| 0 | 34 | 22 | 22 |
| 2 | 30 | 28 | 16 |
| 4 | 23 | 17 | 3 |
| 6 | 17 | 11 | 0 |
| 8 | 13 | 6 | 0 |

The precipitates including the microsporidian spores always showed a high antibacterial activity as compared with that for the supernatant and also maintained their antibacterial activity even after 8 days. Accordingly, it was judged that the microsporidian spores on which an antibiotic was adsorbed were effective as sustained release supports for antibiotics. The diluted supernatants used as controls were prepared by diluting 10 times the supernatant corresponding to the elapsed time of 0 day, as a stock solution, at intervals of 2 days (i.e., the stock solution was diluted 10, 100, 1000 or 10000 times at each elapsed time of 2, 4, 6 and 8 days). If diluting the stock solution 1000 times, the control diluted supernatant lost its antibacterial effect, but the supernatant corresponding to each sample still remained its antibacterial effect. This also indicates that the microsporidian spores are effective for use as sustained release supports for antibiotics.

Example 13

Production of Microsporidian Spores Using Cultured Cells

As insect's cultured cells, there were used the cultured cell line of *Antheraea eucalypti* which was a kind of the Antheraea family and Bm36 cultured cell line originated from lepidopterous insects. The *Antheraea eucalypti* cultured cell line and the Bm36 cultured cell line each was incubated at 26° C. using a culture medium obtained by adding 5% each of the supernatant of domesticated silkworm larva's hemolymphor heat-treated at 60° C. for 15 minutes and fetal calf serum to Grace culture medium. The microsporidian spores were inoculated into the cultured cells according to the following method. More specifically, partially purified microsporidian spores were purified using Percoll, followed by treatment with a 0.2N-KOH solution at 25° C. for 30 minutes, mixing the resulting purified spores and the cultured cells to thus inoculate the spores into the cells.

After 10 days from the inoculation, these cultured cells were harvested, followed by treating the cells with an ultrasonic washing device to thus give a suspension of broken cultured cells, loading the suspension on a Percoll layer and then separating through centrifugation to thus prepare a large amount of microsporidian spores.

Example 14

Non-antigenic chitin beads were prepared by removing the proteins in the cell wall substances of the microsporidian spores similar to those used in Example 1 (*Nosema bombycis*) according to the following method.

First of all, the hydrolysis was performed by repeating 5 cycles in all. In this respect, each cycle comprised a treatment of spores with a 1N NaOH solution maintained at room temperature for 12 hours and a treatment thereof with a 1N HCl solution for additional 12 hours. Thereafter, the spores were finally treated with 95% ethanol for 2 hours to thus dehydrate the spores. Then the spores were precipitated by centrifuging at 2000 rpm for 20 minutes and then water was added to the resulting precipitates. These operations for separating the spores through centrifugation were repeated 7 times to thus give chitin beads from which the proteins as the cell wall substances of the spores were completely removed. To examine the antigen/antibody reaction of the resulting chitin beads through serum reactions, the anti-serum prepared from rabbit using untreated microsporidian spores was used as a test sample, dilute solutions of this anti-serum was used to compare the dilution rate, at which the un-treated spores (sample of the control group) still underwent the serum reaction therewith, to that observed for the treated spores (hydrolyzed sample). The results thus obtained are listed in the following Table 7.

TABLE 7

| | Dilution Rate of Anti-Serum | | | | | | |
|---|---|---|---|---|---|---|---|
| Sample | 16 | 32 | 64 | 128 | 256 | 512 | 1024 |
| Control Sample | + | + | + | + | + | + | + |
| Hydrolyzed Sample | – | – | – | – | – | – | – |

Note):
+: There was observed a serum reaction
–: There was not observed any serum reaction As will be seen from Table 7, in the un-treated spores (sample of the control group), there was observed the serum reaction even at the dilution rate of 1024 times, while the treated spores (hydrolyzed sample) did not undergo any serum reaction at all even at the dilution rate of 16 times. Thus, the proteins among the cell wall substances of the spores which served as antigens were completely removed by the hydrolysis and the resulting chitin beads was accordingly judged to be non-antigenic.

The X-ray diffraction intensity determination also proved that the proteins among the cell wall substances of the microsporidian spores were removed by the acid and/or alkali treatments, while the amount of chitin as the major component relatively increased. When the microsporidian spores embedded in a collodion layer were subjected to X-ray diffraction pattern determination, there are observed diffraction rings (interference rings) of $R_1$, $R_2$, $R_3$ and $R_4$, as will be seen from the foregoing data listed in Table 2, but they are all loose diffraction rings. If only the proteins among the cell wall substances were removed using an acid and/or alkali, however, the intensities of the diffraction patterns $R_1$ to $R_2$ of the chitin present in the treated spores were increased and this clearly indicates that the chitin content of the chitin beads increases.

In addition, when the hydrolyzed sample was reacted with a 1% ninhydrin solution at 25° C. for 20 hours, there was not observed any color reaction at all and this clearly indicates that the sample does not comprise any amino acid at all.

Example 15

Chitin Beads and Chitosan Beads Having Fine Pores

A suspension of the same microsporidian spores (Plestophola M 27) as used in Example 1 was introduced into a 0.2N aqueous potassium hydroxide solution and the resulting mixture was allowed to stand at 25° C. for 30 minutes. After one hour, the resulting sample was neutralized with a phosphate buffer (pH 7.2) of biochemistry grade available from Wako Pure Chemical Industries Co., Ltd. It was confirmed, through observation by a scanning electron microscope, that the cellular substances present in the microsporidian spores were activated by such a simple treatment, the cellular contents were discharged or released from the spores and one pore having a size of about 0.3 μm was formed during such a process. The microsporidian spores obtained after the discharge of the intracellular substances each was an elliptic sphere having a size of 1.7 μm (major axis)×0.9 μm (minor axis) and a thickness of the cell membrane of about 0.13 μm and wherein an entire vacant space was formed within the cell wall and the pore formed after the discharge of the intracellular substances was positioned at one end of the elliptic sphere along the major axis. The presence of such a pore easily permits the encapsulation of, for instance, enzymes, antibiotics, metal ions, medicines, viruses and biologically active substances within the inner vacant spaces of the microsporidian spores by reducing the environmental pressure around the microsporidian spores or releasing the reduced pressure. Therefore, the chitin beads and the chitosan beads according to the present invention are uniform in their size and in finely particulate states and are useful as sustained release supports for these pharmaceutically effective components.

Example 16

Chitin Beads and Chitosan Beads Having Fine Pores

The same procedures as used in Example 15 were repeated except that *Nosema bombycis* No. 520 was substituted for the microsporidian spores used in Example 15. The microsporidian spores thus obtained after the discharge of intracellular substances each was an elliptic sphere having a size of 2.6 μm (major axis)×1.4 μm (minor axis) and a thickness of the cell membrane of about 0.13 μm and wherein an entire vacant space was formed within the cell wall and it was confirmed, through observation by a scanning electron microscope, that one pore having a size of about 0.1 μm was formed at one end of the elliptic sphere along the major axis thereof. The chitin beads and chitosan beads according to the present invention would be effective as sustained release supports for pharmaceutically effective components like the beads of Example 15, due to the presence of such a pore in each spore.

Example 17

The safety of the microsporidian spores from which only the proteins among the cell wall substances thereof were removed was examined according to the following method.

A spore suspension ($4\times10^8$ spores/ml) prepared by subjecting the microsporidian spores prepared in Example 1 to hydrolysis using an acid was intravenously injected 4 times to each rabbit at intervals of one week, followed by observation of the growing process of the rabbit. After 6 months from the inoculation, neither weight change abnormality nor appearance abnormality of the treated rabbits into which the spores had been injected were not observed at all, like the control rabbits free of any spore injection.

Industrial Applicability

The chitin beads and the chitosan beads having the uniform and fine particle size according to the present invention can be used as carriers for drug-delivery systems as well as base materials for cosmetic foundations. Moreover, if enzymes, living cells or the like are adhered to or immobilized on the chitosan beads, the resulting product may be used to constitute a bioreactor effective in food industries and other various industrial fields.

If an enzyme or an immunological antibody is linked to the surface or interior of the beads or the both, the resulting product can be used as, for instance, an immunological carrier. Moreover, modified chitin beads which are modified by converting the chitin moiety thereof into glycol chitin and carboxymethyl chitin are excellent in moisture retention properties and therefore, can be used as materials for cosmetics. Moreover, if a vinyl compound or the like is grafted on the microsporidian spore or the chitin beads and then an enzyme is immobilized on the grafted chitin beads, the resulting product not only permits the improvement in the stability of the enzyme activity, but also permits the exhibition of still further efficient enzyme activity while making the most use of characteristic properties of the fine particles having a very large effective surface area.

The chitin beads and the chitosan beads according to the present invention, which are subjected to a treatment for removing the proteins present therein, are free of any antigen/antibody reaction even when embedding them in animal bodies including human bodies and therefore, they can be used as sustained release carriers. Moreover, the chitin beads and the chitosan beads would be decomposed or degradated by the action of the enzymes present in the bodies after the lapse of a certain time period and therefore, can be used as safe materials capable of being decomposed or degradated in living bodies. The chitin beads and the chitosan beads hardly serve as antigens even when they are embedded in living biological tissues. For this reason, the chitin beads and the chitosan beads may be used by immobilizing a drug having physiological actions and embedding the drug-immobilized beads in living bodies. In particular, the chitin beads and the chitosan beads in which a medicine showing an anti-cancer effect is encapsulated may be used in a frontier medical field as missile carriers.

The chitin beads and the chitosan beads according to the present invention may be hollow beads which comprise vacant spaces therein and in this case, a fine pore or fine pores are formed on and/or through the cell wall tissue. Accordingly, living cells, bacteria, antibiotics, biologically active substances or the like may be introduced into the vacant spaces through these fine pores. The substances encapsulated into the beads are not easily affected by external factors for modifying proteins (such as ultraviolet light rays) and thus these beads permit the maintenance of the biological activity of the substances over a long time period. Thus, these beads can also be used as novel materials for protecting, for instance, natural enemy microorganisms.

The microsporidian spores according to the present invention are also excellent as base materials for microcapsules for encapsulating medicines, physiologically active substances, hormones, vaccines or the like and microcapsules in which, for instance, agricultural chemicals or fertilizers are encapsulated into the microsporidian spores may be used as soil conditioners. In addition, those obtained by encapsulating feed components may be used as feeds for domestic animals or those for pisciculture.

Moreover, according to the present invention, these beads permit the easy control of the sustained release rate, the sustained release amount and the degree of biodegradation of substances such as medicines, physiologically active substances and antibiotics, by adjusting the degree of the hydrolysis, or by controlling the degree of fine pores formed on the cell wall of the microsporidian spores. Furthermore, the chitin beads and the chitosan beads may likewise be used as biodegradable materials since they are gradually decomposed by the enzymes present in the living bodies.

What is claimed is:

1. Chitin beads which are microsporidian spores proliferated in insect bodies or cultured cells, said spores having a uniform and fine particle size and having a cell wall substance mainly composed of chitin.

2. The chitin beads as set forth in claim 1 wherein the chitin beads are those from which the proteins are removed and which are thus non-antigenic.

3. The chitin beads as set forth in claim 1 wherein the proliferated microsporidian spores are those having pores formed through or on the cell walls and wherein the chitin beads are hollow beads.

4. Chitosan beads which are N-deacetylated chitin beads in which said chitin beads are microsporidian spores proliferated in insect bodies or cultured cells, said spores having a uniform and fine particle size and having a cell wall substance mainly composed of chitin, and the chitin as the major cell wall substance is subjected to N-deacetylation.

5. The chitosan beads as set forth in claim 4 wherein the chitosan beads are those from which the proteins are removed and which are thus non-antigenic.

6. The chitosan beads as set forth in claim 4 wherein the proliferated microsporidian spores are those having pores formed through or on the cell walls and wherein the chitosan beads are hollow beads.

7. A carrier which is chitin beads or chitosan beads, said chitin beads being microsporidian spores proliferated in insect bodies or cultured cells, said spores having a uniform and fine particle size and having a cell wall substance mainly composed of chitin, said chitosan beads being obtained by subjecting the chitin constituting the major cell wall substance to N-deacetylation.

8. The carrier as set forth in claim 7 wherein the chitin beads and the chitosan beads are those from which the proteins are removed and which are thus non-antigenic.

9. The carrier as set forth in claim 7 wherein the proliferated microsporidian spores are those having pores formed through or on the cell walls and wherein the chitin beads and the chitosan beads are hollow beads.

10. The carrier as set forth in claim 7 wherein the carrier is used for immobilization or introduction of a physiologically active substance, an antibiotic, a living cell, a microorganism, a dye, a medicine, an agricultural chemical, a perfume, a feedstuff or a foodstuff.

11. A method for producing chitin beads having a uniform and fine particle size comprising the steps of proliferating microsporidian spores by orally or percutaneously inoculating the spores into insect bodies in a concentration of $5\times10^2$ to $5\times10^8$ spores/ml, harvesting the proliferated microsporidian spores from the grown insect bodies and then purifying the resulting spores to give chitin beads as uniform fine particles.

12. The method for producing chitin beads having a uniform and fine particle size as set forth in claim 11 wherein the time for inoculating the spores into insect bodies is just after 2nd instar silkworm larvae stage and the grown insect are 5th instar silkworm larvae.

13. The method for producing chitin beads having a uniform and fine particle size as set forth in claim 11 wherein the insect is a larva of domesticated silkworm.

14. A method for producing chitosan beads having a uniform and fine particle size comprising the steps of proliferating microsporidian spores by orally or percutaneously inoculating the spores into insect bodies in a concentration of $5\times10^2$ to $5\times10^8$ spores/ml, harvesting the proliferated microsporidian spores from the grown insect bodies, purifying the resulting spores to give chitin beads having a uniform and fine particle size and then subjecting the chitin beads to N-deacetylation to give chitosan beads.

15. The method for producing chitosan beads having a uniform and fine particle size as set forth in claim 14 wherein the time for inoculating the spores into insect bodies is just after 2nd instar silkworm larvae stage and the grown insects are 5th instar silkworm larvae.

16. A method for producing microsporidian spores comprising the steps of adding cultured cells derived from an insect to a cell culture medium which contains 5 to 50% by weight of a supernatant of hemolymphor of domesticated silkworm larvae, inoculating microsporidian spores into the culture medium to thus proliferate the spores and isolating the microsporidian spores from the proliferated cells.

* * * * *